United States Patent
Oppelt (10) Patent No.: US 6,269,052 B1
(45) Date of Patent: Jul. 31, 2001

(54) TRANSMITTING/RECEIVING CIRCUIT AND TRANSMITTING/RECEIVING METHOD FOR A TRANSDUCER

(75) Inventor: Ralph Oppelt, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/375,069

(22) Filed: Aug. 16, 1999

(30) Foreign Application Priority Data

Aug. 14, 1998 (DE) ............................................. 198 36 997

(51) Int. Cl.$^7$ ...................................................... H04B 1/40
(52) U.S. Cl. ............................................. 367/135; 367/903
(58) Field of Search .................................... 367/135, 903; 600/437, 447; 73/629, 632

(56) References Cited

U.S. PATENT DOCUMENTS

| | | | |
|---|---|---|---|
| 5,199,299 | * | 4/1993 | Hughes et al. ........................ 367/903 |
| 5,269,189 | * | 12/1993 | Thompson et al. ..................... 73/632 |
| 5,603,324 | * | 2/1997 | Oppelt et al. ..................... 128/660.01 |
| 6,050,945 | * | 4/2000 | Peterson et al. ....................... 600/443 |

FOREIGN PATENT DOCUMENTS 195 14 330A1   11/1995  (DE) .

* cited by examiner

Primary Examiner—Ian J. Lobo
(74) Attorney, Agent, or Firm—Herbert L. Lerner; Laurence A. Greenberg; Werner H. Stemer (57) ABSTRACT

The circuit and the method serve to transmit a transmission signal to a transducer and to receive a reception signal from the transducer. The transmitter and the receiver are each alternatively coupled to the transducer and decoupled from one another. The coupling and decoupling is thereby achieved by a total of three nonlinear two-terminal networks (Z1, Z2, Z3). The transmitter is connected to the transducer via a bipolar voltage limiter and the receiver is connected to the transducer via a bipolar current limiter.

17 Claims, 4 Drawing Sheets

TRANSMITTING/RECEIVING CIRCUIT AND TRANSMITTING/RECEIVING METHOD FOR A TRANSDUCER

BACKGROUND OF THE INVENTION

FIELD OF THE INVENTION

The invention lies in the electronics field. Specifically, the invention relates to a circuit having a transmitter for transmitting a transmission signal to a transducer and a receiver for receiving a reception signal from the transducer. In addition, the invention relates to a method for transmitting a transmission signal to a transducer and for receiving a reception signal from the transducer.

In particular, the invention also relates to a transmitting/receiving circuit, which is also referred to as a transceiver circuit, as well as a transmitting/receiving method for an ultrasonic transducer.

Ultrasonic transducers are usually operated in the so-called pulse echo method. Such transducers must accordingly be able to transmit and to receive alternately. An ultrasonic transducer of this type may be constructed from one or more piezoelectric individual elements arranged for example in a linear or else in a two-dimensional array. In the transmission mode, these individual elements are excited to produce high-frequency oscillations by means of electrical transmission signals which may, if appropriate, be offset in terms of their phase angle with respect to one another for each individual element. As a result, an ultrasonic pulse is generated and is radiated into an examination object to be imaged. The precise focus region of the ultrasonic pulse in the examination object can be varied by way of the driving of the piezoelectric individual elements of the ultrasonic transducer. The ultrasonic pulse is reflected within the examination object in the direction of the ultrasonic transducer. The reflection can occur for example at discontinuities in the examination medium such as e.g. interfaces between materials of different acoustic impedance. These echo pulses or reflected pulses are received by the transducer or the individual elements and converted into a corresponding electrical reception signal. That signal is fed to a receiver equipped with a very sensitive preamplifier in order to raise the signal level of the reception signal. The signal level is generally very low. The amplified reception signal can then be forwarded to a signal processor for evaluation of the information content and for generation of a pictorial representation.

In order to ensure efficient functioning, the transmission signal and the reception signal must be isolated from one another. Therefore, each transducer element is connected to a transmitting/receiving circuit which electrically connects the transducer element selectively either to the transmitter or to the receiver. A transmitting/receiving circuit of this type is also referred to as a transmit/receive separator.

The decoupling of the transmitter from the receiver is desirable in principle because the amplitudes of the transmitted and received signals differ very greatly from one another. A transducer element is typically excited with a signal level of more than 100 V. A reception signal reflected from the examination object, on the other hand, has a very low voltage amplitude in the mV range. The transmitting/receiving circuit decouples receiver and transmitter from one another in order to avoid damage to the sensitive preamplifier in the receiver caused by the powerful transmission signal during the transmission mode. In addition, the decoupling during the transmission mode prevents undesirable influencing of the transmission signal, for example in the form of distortion, by the receiver. On the other hand, decoupling of receiver and transmitter is also desirable during the reception mode, in order to keep transmitter noise away from the receiver.

Various transmitting/receiving circuits are known. The changeover and decoupling can be performed by a circuit either actively, that is to say under the control of a switching signal, or else passively, that is to say automatically. An active transmitting/receiving circuit normally contains a plurality of active components such as transistors which vary their properties in dependence on the switching signal present at a control input. However, an active transmitting/receiving circuit always requires a separate control line for each individual element of the ultrasonic transducer, via which control line the switching signal is transmitted. Moreover, an additional control circuit is required which synchronizes the changeover and decoupling with the transmission and reception signals. If synchronization fails, there is the risk that sensitive assemblies in the receiver will be destroyed. Passive implementations of a transmitting/receiving circuit are usually either limited in terms of their dynamic range or they comprise complicated components, such as, for example transformers with a plurality of windings and taps.

An earlier, commonly assigned German patent application DE 195 14 330 A1 discloses a transmitting/receiving circuit for an ultrasonic imaging system in which a transducer is optionally electrically connected to a transmitter in a transmission mode and to a receiver in a reception mode. For this purpose, the transmitting/receiving circuit contains at least one variable-capacitance diode connected in the reverse direction for the transmission signal of the transmitter between the transducer and receiver. Instead of a single variable-capacitance diode, it is also possible to provide a reverse-connected series circuit borne by two variable-capacitance diodes. When a variable-capacitance diode is used, however, it is possible for a high current pulse to be coupled into the receiver, particularly in the event of a steep rise in the transmission signal. This current pulse can then result in damage to the receiver.

SUMMARY OF THE INVENTION

It is accordingly an object of the invention to provide a transceiver circuit and a transmit/receive method, which overcomes the above-mentioned disadvantages of the heretofore-known devices and methods of this general type and which can be constructed using simpler means in comparison with the prior art implementations. It is a particular object to avoid having to use complicated components such as separate control lines or else transformers. In addition, it is also an object to reliably protect the receiver against the powerful transmission signal.

With the foregoing and other objects in view there is provided, in accordance with the invention, a circuit configuration, comprising:

a transmitter for transmitting a transmission signal, a transducer connected to the transmitter for receiving the transmission signal, and a receiver having an input connected to the transducer for receiving a reception signal from the transducer;

a first nonlinear, bipolar voltage-limiting two-terminal network connected between the transmitter and the transducer;

a second nonlinear, bipolar current-limiting two-terminal network connected between the transducer and the receiver; and a third nonlinear, bipolar voltage-limiting two-terminal network connected in parallel with the input of the receiver.

With the above and other objects in view there is also provided, in accordance with the invention, a method of transmitting a transmission signal to a transducer and for receiving a reception signal from the transducer, which comprises:

coupling a transmission signal of a transmitter to a transducer via a first nonlinear two-terminal network and decoupling the transmission signal from a receiver with a second and a third nonlinear two-terminal network; and coupling a reception signal of the transducer to a receiver via the second and third nonlinear two-terminal networks and decoupling the reception signal from the transmitter with the first nonlinear two-terminal network; and thereby limiting a voltage present at the first nonlinear two-terminal network and a voltage present at the third nonlinear two-terminal network in bipolar fashion; and limiting a current flowing through the second nonlinear two-terminal network in bipolar fashion.

The invention is based on the insight that a transceiver circuit can be realized in a simple manner by connecting together three nonlinear two-terminal networks and the transducer. The specification that the third nonlinear two-terminal network is connected in parallel with the input of the receiver is in this case to be understood to mean that the third nonlinear two-terminal network is connected in parallel with an input impedance of the receiver. The first and third nonlinear two-terminal networks then constitute virtually a short circuit for large signal amplitudes and virtually an open circuit for small signal amplitudes. The second nonlinear two-terminal network, on the other hand, constitutes virtually a short circuit for small signal amplitudes and virtually an open circuit for large signal amplitudes. An open circuit means a very high-impedance state in this context.

The effect that is achieved, then, by the described nonlinear behavior of the three two-terminal networks is that the transmitter and the receiver are alternately coupled to the transducer and in each case decoupled from one another. During the transmission mode, only the transducer is coupled to the transmitter, whereas the receiver is decoupled from the transmitter. This prevents the sensitive input electronics for amplifying small signal amplitudes in the receiver from being destroyed by the high signal amplitudes of the transmission signal. On the other hand, an undesirable perturbation from the receiver acting on the transmitter, the perturbation distorting the transmission signal under certain circumstances, is also avoided by virtue of the decoupling. During the reception mode, on the other hand, the three nonlinear two-terminal networks have the effect that the transducer is coupled only to the receiver and is decoupled from the transmitter. The reception signal having a signal amplitude which is very low in any case is thereby conducted only to the intended destination, the receiver. Practically no part of the low received power is lost in the path of the circuit which leads to the transmitter. This improves the efficiency of the circuit.

The first and third nonlinear two-terminal networks are voltage limiters. In addition, an embodiment in which the second nonlinear two-terminal network effects current limiting is also preferred. In both embodiments, the voltage and current limiting is in each case designed in a bipolar fashion. This is to be understood to mean that the first and third nonlinear two-terminal networks limit the voltage to a positive limit voltage in the case of positive current values and to a negative limit voltage, which essentially corresponds to the positive limit voltage except for the sign, in the case of negative current values. Conversely, the second nonlinear two-terminal network effects limiting to a positive limit current in the case of a voltage of greater than zero and limiting to a negative limit current in the case of a voltage of less than zero. In this case, in contrast to the variable-capacitance diodes used in the prior art, the current is genuinely limited to a maximum or minimum value. As a result, the receiver is reliably protected against undesirable current spikes and thus against destruction.

A transition region between positive and negative limit voltages, or positive and negative limit currents is in each case designed to be as steep as possible in order to minimize losses during the changeover between positive and negative signal amplitudes.

The voltage or current limiting of the three nonlinear two-terminal networks is designed in such a way that the signal amplitude of the transmission signal lies beyond the limit voltage or the limit current, respectively, and the signal amplitude of the reception signal lies within an interval formed by the positive and negative limit voltages or the positive and negative limit currents, respectively. The above-described automatic decoupling of transmitter and receiver is thus produced both in the transmission mode and in the reception mode. Moreover, the transducer is likewise automatically coupled in each case to the correct circuit section, that is to say to the transmitter or to the receiver. An active changeover by means of a control signal is not required for this.

In this context, a transducer is understood to mean any component which is driven by means of a signal having a high signal level and reacts to it indirectly with a response signal having a comparatively small signal amplitude. The response signal is in this case effected by this driving. The difference between the signal level of the driving signal (=transmission signal) and the response signal (=reception signal) is in this case at least two orders of magnitude. An electroacoustic transducer, a transmitting/receiving antenna for electromagnetic radiation and also a resonator are examples of components which fall into the category described above.

In accordance with an added feature of the invention, the transducer is an ultrasonic transducer. Such an ultrasonic transducer emits acoustic waves into an examination zone, and receives reflected signals from said zone, which signals then enable conclusions to be drawn concerning the nature of the examination zone. An ultrasonic transducer is driven by transmission signals having a high signal amplitude and supplies reception signals having a low signal amplitude, with the result that corresponding decoupling of circuit sections which are intended for the respective case of operation is advantageous. In this case, the ultrasonic transducer may be constructed either from a single sound-emitting element or else from a plurality of such individual elements.

In this case, it is then possible to provide, in particular for each individual element, a separate transceiver circuit for feeding in the respective transmission signal and for conducting away the respective reception signal.

In accordance with an additional feature of the invention, the transducer, in particular the ultrasonic transducer has a contact which is connected to system ground. This variant enables the number of connection terminals and lines required to be reduced. This is because then, preferably, in the case of an ultrasonic transducer having a plurality of individual elements, one of the two contacts of each individual element can be connected to a common ground connection. The latter is then designed, in particular, as a contact layer extending over all the individual elements. This simplifies the structure of the ultrasonic transducer. In contrast to this, in the case of a floating, that is to say ungrounded, connection of the ultrasonic transducer, within the circuit, two separate connection terminals and lines are provided for each transducer element. The resulting number of connection terminals and lines is thus practically twice as large as in the case of the variant with single-ended grounding.

In accordance with another feature of the invention, the first, second and third nonlinear two-terminal networks are passive two-terminal networks. This is to be understood to mean that the three nonlinear two-terminal networks have no connection at all to a supply voltage nor, in particular, to the system ground. Such a connection otherwise leads to a ground loop that might result in an undesirable circuiting current. This would, however, impair the overall behavior of the transmitting/receiving circuit.

In accordance with a further feature of the invention, the transmitter has an output, and a fourth nonlinear two-terminal network is connected in parallel with the output of the transmitter, i.e., a fourth nonlinear two-terminal network is provided at the output of the transmitter. The fourth nonlinear two-terminal network is connected in parallel with the output, that is to say in parallel with an output impedance of the transmitter. This embodiment affords advantages particularly when the fourth nonlinear two-terminal network is also embodied with bipolar current limiting. This is because a transformer can be provided within the transmitter, at the output, and this transformer transforms the transmission signal to its final, high signal level. The fourth nonlinear two-terminal network then conducts away a current which is still stored in a secondary winding of the transformer after the transmission signal has been transmitted. The decay time of the transmission signal is considerably reduced as a result of this. However, there are also other embodiments of the transmitter in which no transformer is provided at the output. In these cases, it is then also possible to dispense with the fourth nonlinear two-terminal network at the output of the transmitter.

In accordance with again an added feature of the invention, the fourth nonlinear two-terminal network is a two-terminal network with bipolar current limiting.

In accordance with again an additional feature of the invention, the fourth nonlinear two-terminal network is a passive network.

In accordance with again another feature of the invention, the second two-terminal network with bipolar current limiting comprises a series circuit formed by a first normally-on MOSFET having a first gate terminal, a first source terminal, and a first drain terminal, and a second normally-on MOSFET having a second gate terminal, a second source terminal, and a second drain terminal, wherein the first MOSFET and the second MOSFET are arranged with mutually opposite polarity within the series circuit, and including a feedback via a resistance from the first gate terminal and the second gate terminal to the first and second source terminals, respectively.

In accordance with yet an additional feature of the invention, the first gate terminal is electrically connected to the second drain terminal for feeding back the first gate terminal via a drain-source resistance of the second MOSFET to the first source terminal, and the second gate terminal is electrically connected to the first drain terminal for feeding back the second gate terminal via a drain-source resistance of the first MOSFET to the second source terminal.

With regard to the above-described embodiments of the circuit, respectively corresponding configurations exist for the method. Accordingly, the configurations of the method also have the same advantages as the respectively corresponding embodiments of the circuit.

A further embodiment of the circuit relates to the configuration of the second and fourth nonlinear two-terminal networks as a bipolar current limiter in each case. In this design, the two-terminal network with bipolar current limiting comprises two normally on MOSFETs (Metal Oxide Semiconductor Field Effect Transistor), where a gate terminal of each MOSFET is fed back via a resistance to a source terminal. By virtue of this feedback, each of the two MOSFETs acts as a unipolar current limiter. The MOSFETs having feedback in this way could also be referred to as unipolar current sources. Connecting the two MOSFETs having feedback in series with mutually opposite polarity then produces a nonlinear two-terminal network in which one MOSFET having feedback carries out current limiting to a positive limit current for a first voltage polarity and the other MOSFET having feedback carries out current limiting to a negative limit current for the opposite voltage polarity. Overall, the desired bipolar current limiting is then present. The limit current is set by way of the resistance.

The series circuit of the two MOSFETs described is also able, inter alia, to limit the current in a bipolar fashion because the respective MOSFET that is not currently being operated as a current limiter passes the limit current of the other transistor via a backward diode. This backward diode is an inherent feature of normally-on MOSFETs.

The current-limiting effect of the two MOSFETs is beneficial for the high signal levels of the transmission signal. However, the low signal levels of the reception signal drive the two MOSFETs in each case only within a small region around the zero point in the family of output characteristic curves. In this small drive range, a normally on MOSFET acts virtually as a linear resistor both for positive and negative signal amplitudes. This explains the decoupling effect of the interconnection.

Although the described configuration of the second and fourth nonlinear two-terminal networks with the two normally-on MOSFETs actually comprises active components, what is involved is nevertheless a passive two-terminal network. This is because both MOSFETs are operated passively. At no point is an operating or supply voltage fed in via a supply line, for example for setting the operating point. Moreover, the nonlinear two-terminal network does not comprise a connection to the system ground either. Consequently, this design of the second nonlinear two-terminal network is both passive and ungrounded (floating).

In accordance with again a further feature of the invention, the resistance is a common feedback impedance connected between the first and second source terminals and between the first and second gate terminals and the first and second source terminals. In other words, there is provided just a single feedback impedance for the two normally-on MOSFETs. The impedance is situated in the feedback path both of the first and of the second MOSFET. The positive and also the negative limit current are set by way of the impedance. Since the feedback impedance also critically influences the gradient of the characteristic curve of the nonlinear two-terminal network in the transition region between positive and negative limit current as well, it is advantageous to use, instead of a respective impedance for the positive and negative limit currents, just a single impedance for both polarities. This increases the gradient of the characteristic curve in the transition region, thereby resulting in a concomitant reduction in losses at the same time.

Depending on the frequency range in which the nonlinear two-terminal network is to be operated for the purpose of current limiting, in accordance with yet an added feature of the invention, the common feedback impedance is a (non-reactive) resistive, inductive, capacitive, or arbitrarily complex impedance. In this case, a purely resistive design is better suited to broadband applications, whereas a reactive or complex design of the impedance is preferred for narrowband applications.

In a further embodiment variant, the nonlinear two-terminal network, for the purpose of current limiting, comprises the two normally-on MOSFETs and no further component, in particular no separate impedance either. In this embodiment variant, the two normally on MOSFETs each have feedback via a drain-source resistance of the respective other MOSFET. In this context, the drain-source resistance is then to be understood to mean the nonlinear resistance of said backward diode. Consequently, this embodiment variant manages with a minimal use of components.

In accordance with yet an additional feature of the invention, the transducer is excited with the transmission signal and the transducer emits ultrasound in response.

In accordance with yet another feature of the invention, the transducer is connected to system ground.

In accordance with yet a further feature of the invention, the first, second and third nonlinear two-terminal networks are each purely passive two-terminal networks.

In accordance with yet again a further feature of the invention, a decay time of the transmission signal is shortened at the transmitter with a fourth nonlinear two-terminal network.

In accordance with a concomitant feature of the invention, a current flowing through the fourth nonlinear two-terminal network is limited in bipolar fashion.

Other features which are considered as characteristic for the invention are set forth in the appended claims.

Although the invention is illustrated and described herein as embodied in a transmitting/receiving circuit and transmitting/receiving method for a transducer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings. It will be noted, with regard to the accompanying drawings, that the views in the drawing are not to scale and certain features are illustrated diagrammatically.

BRIEF DESCRIPTION OF THE DRAWINGS:

Each of the corresponding parts are provided with the same reference symbols in FIGS. 1 to 9.

DESCRIPTION OF THE PREFERRED EMBODIMENTS

Figure 1:
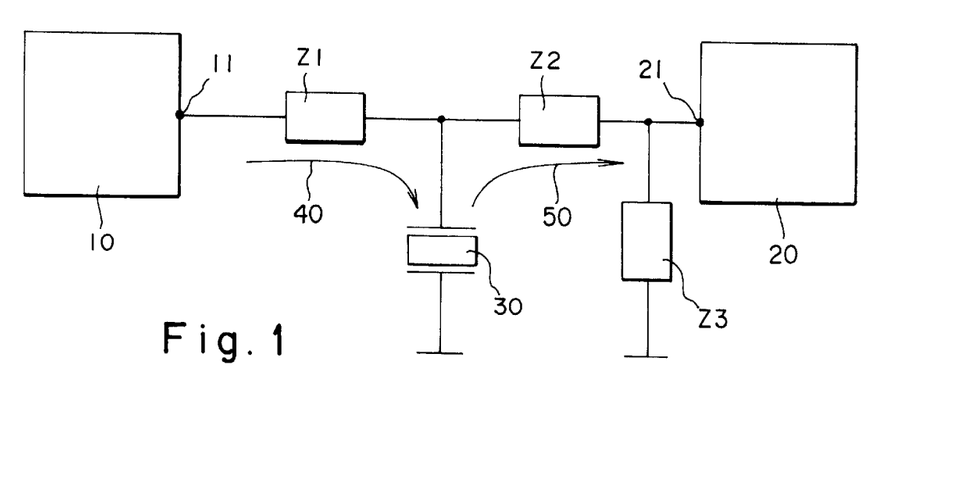
FIG. 1 is a schematic block diagram illustrating a transmitting/receiving circuit with three nonlinear two-terminal networks and a transducer.

Referring now to the figures of the drawing in detail, wherein corresponding parts are identified with corresponding reference numerals throughout, and first, particularly, to FIG. 1 thereof, there is seen a circuit for transmitting a transmission signal 40 to a transducer 30 and for receiving a reception signal 50 from the transducer 30. The transmission signal 40 is thereby fed from a transmitter 10 via a first nonlinear two-terminal network Z1 to the transducer 30, which is grounded at one end. The transducer 30 is a piezoelectric ultrasonic transducer which, on account of the electrical transmission signal 40, is excited to effect acoustic oscillations and thus to emit sound waves into a non-illustrated examination zone. The emitted sound waves are reflected in the examination zone and converted back into an electrical reception signal 50 by the transducer 30.

The transducer 30 may be implemented as a single-element ultrasonic transducer or else as a multi-element ultrasonic transducer array. In the latter case, a separate circuit in accordance with the illustration of FIG. 1 may be provided for each transducer element.

The received signal 50 is transmitted to a receiver 20 via a second nonlinear two-terminal network Z2. Since the reception signal 50 has only a very low signal level, the receiver 20 contains a sensitive input amplifier (likewise not illustrated) which correspondingly raises the signal level. This is followed, in the receiver 20, by a further signal processing arrangement and, if appropriate, a unit for pictorially representing the reception signal 50.

The signal levels of the transmission signal 40 and of the reception signal 50 differ considerably. While the transmission signal 40 is present as a bipolar transmission pulse with peak voltage values of up to a few 100 V, in this case of ±100 V, the absolute signal level of the reception signal 50 assumes a maximum value of up to 1 volt, for example just a few millivolts (mV). There are also corresponding power differences between the transmission and reception signal 40 and 50, respectively.

The circuit illustrated in FIG. 1 also ensures, therefore, that the powerful transmission signal 50 does not reach the receiver 20, where it would otherwise damage the sensitive input amplifier. On the other hand, the transmitter 10 is decoupled from the transducer 30 when a reception signal 50 is supplied by the transducer 30. To afford reliable protection against the powerful transmission signal 40, a third nonlinear two-terminal network Z3 is connected in parallel at an input 21 of the receiver 20. The third nonlinear two-terminal network effects a virtual short circuit of the input 21 for high signal levels.

Figure 2:
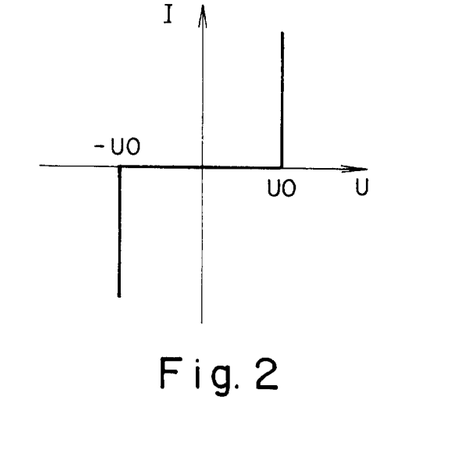
FIG. 2 is a graph of an idealized characteristic curve of the first and third nonlinear two-terminal networks.
Figure 3:
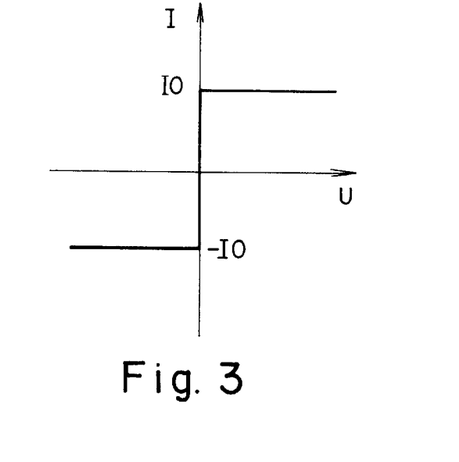
FIG. 3 is a graph of an idealized characteristic curve of the second nonlinear two-terminal network.

The first and third nonlinear two-terminal networks Z1 and Z3, respectively, are each embodied as bipolar voltage limiters, and the nonlinear two-terminal network Z2, on the other hand, is embodied as a bipolar current limiter. With reference to FIGS. 2 and 3, there are shown idealized characteristic curves of the bipolar voltage-limiting two-terminal networks Z1 and Z3 and of the bipolar current-limiting two-terminal network Z2, respectively.

With reference to FIG. 2, a voltage U present in the nonlinear two-terminal networks Z1 and Z3 is limited to a limit voltage U0. The positive limit voltage U0 is dropped across the nonlinear two-terminal network Z1 or Z3 in the case of a positive current I and the negative limit voltage −U0 in the case of a negative current I. Conversely, in accordance with the characteristic curve illustrated in FIG. 3, the second nonlinear two-terminal network Z2 effects bipolar limiting of a current I to a limit current I0. A positive limit current I0 flows in the case of a positive voltage U and a negative limit current −I0 flows in the case of a negative voltage U.

A transition between positive and negative limit voltage +U0 and −U0, respectively, and between positive and negative limit current +I0 and −I0, respectively, is abrupt in the idealized characteristic curves illustrated in FIGS. 2 and 3. The abrupt transitions thereby correspond to a vanishing junction conductance and junction resistance. Of course, these vanishing values cannot be obtained in practice. However, a transition region which approximates as far as possible to the profile of the idealized characteristic curve is sought in a practical realization.

Figure 4:
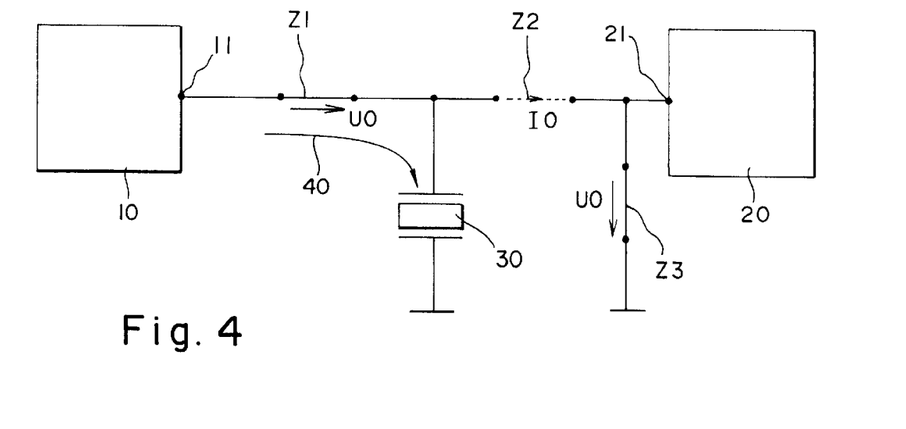
FIG. 4 is a schematic block diagram of the transceiver circuit of FIG. 1 in the transmission mode.
Figure 5:
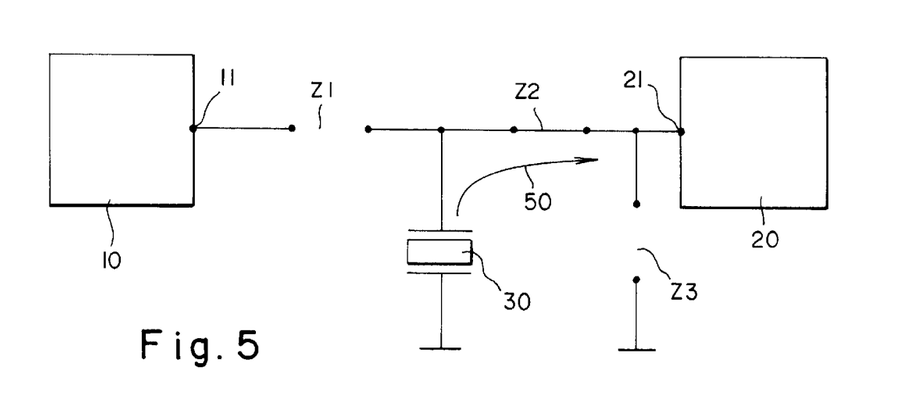
FIG. 5 is a similar view thereof in the reception mode.

Taking the current- and voltage-limiting behavior of the three nonlinear two-terminal networks Z1 to Z3 into consideration, it is now possible to specify equivalent circuit diagrams for the circuit in accordance with FIG. 1 for the respective case of operation. FIG. 4 illustrates the transmission mode, whereas FIG. 5 shows the reception mode. During the transmission mode, the transmitter 10 generates the transmission signal 40 at its output 11. The signal level of the transmission signal 40 is thereby considerably higher than the limit voltage U0 of the first and third nonlinear two-terminal networks Z1 and Z3, respectively. This limit voltage U0 lies between approximately 0.7 V and approximately 1 V, depending on the components used and the ultimately effective signal levels of the transmission signal 40. The first and third nonlinear two-terminal networks Z1 and Z3, respectively, thus constitute virtually a short circuit for the high-level transmission signal 40. The second nonlinear two-terminal network Z2, on the other hand, effects limiting of the current flowing through it to the limit current I0, which is subsequently conducted to ground via the third nonlinear two-terminal network Z3.

Consequently, the input 21 of the receiver 20 is decoupled from the transmitter 10.

For current amplitudes which are larger than the limit current I0, the second nonlinear two-terminal network Z2 constitutes an open circuit, with the result that most of the transmission signal 40 is conducted into the transducer 30, where it is converted into acoustic radiation. A limit current I0 which is as small as possible evidently has a positive effect on the losses. This is because the smaller the set limit current I0, the smaller the portion of the transmission signal 40 that is conducted past the transducer 30. The decoupling described also means that the receiver 20 cannot influence the transmission signal 40 in a distorting manner.

During the reception mode illustrated in FIG. 5, in which the transducer 30 generates an electrical reception signal 50 having a very low signal level, in particular below the limit voltage U0 and below the limit current I0, the first and third nonlinear two-terminal networks Z1 and Z3, respectively, constitute virtually an open circuit. During the reception mode, the signal amplitudes, in particular the voltage amplitudes, are so small that the second nonlinear two-terminal network Z2 is operated precisely in the transition region of the characteristic curve illustrated in FIG. 3. This transition region ideally constitutes a short circuit. In reality, at least a very low junction or forward resistance is sought in this case. The steeper the characteristic curve is designed at this point, the lower, once again, the losses turn out to be.

Figure 6:
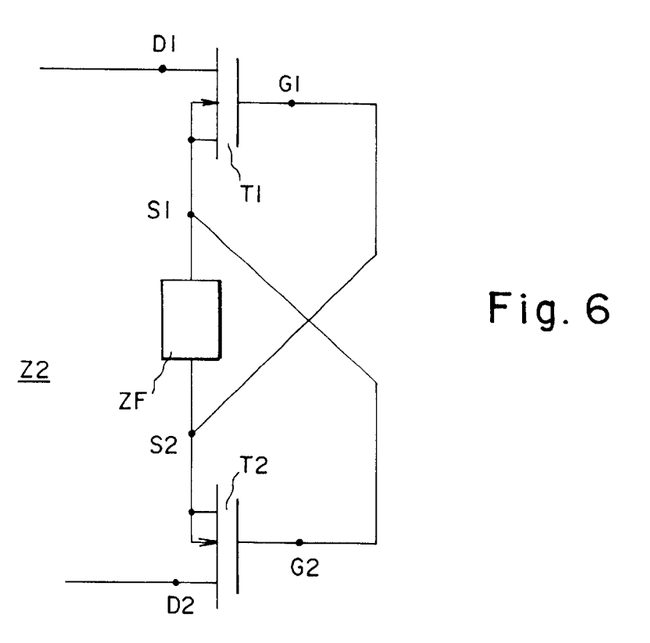
FIG. 6 is a schematic diagram of an embodiment of the second nonlinear two-terminal network.

FIG. 6 illustrates one possible implementation of the second nonlinear two-terminal network Z2. It essentially comprises a first normally-on MOSFET (Metal Oxide Semiconductor Field Effect Transistor) T1 having a first gate terminal G1, a first source terminal S1 and a first drain terminal D1, and also a second normally-on MOSFET T2 having a second gate terminal G2, a second source terminal S2 and a second drain terminal D2. The two MOSFETs T1 and T2 are both of the same conduction type, the n-type in the present case. The current-limiting effect of the second nonlinear two-terminal network Z2 is achieved by virtue of the fact that both the first gate terminal G1 is fed back via a feedback impedance ZF to the first source terminal S1 and the second gate terminal G2 is fed back via the same feedback impedance ZF to the second source terminal S2. The first MOSFET T1 thereby effects current limiting in the case of positive voltage values and the second MOSFET T2 effects current limiting in the case of negative voltage values, in each case referring to a voltage arrow directed from the first drain terminal D1 to the second drain terminal D2.

The first and second MOSFETs T1 and T2, respectively, are connected in series via the feedback impedance ZF. For this purpose, the first source terminal S1 of the first MOSFET T1 and the second source terminal S2 of the second MOSFET T2 are in each case connected to one of the two connections of the feedback impedance ZF. Furthermore, the first gate terminal G1 is connected to the second source terminal S2 and the second gate terminal G2 is connected to the first source terminal S1. Consequently, the two MOSFETs T1 and T2 are arranged with mutually opposite polarity within the series circuit of the second nonlinear two-terminal network Z2. The connections of the two-terminal network Z are formed by the first and second drain terminals D1 and D2, respectively.

Compared with another circuit variant, in which each of the two MOSFETs T1 and T2 is assigned a separate feedback impedance ZF, the variant illustrated in FIG. 6 has a lower junction or forward resistance. In accordance with the above explanations, this is particularly advantageous for the present application.

The positive and also the negative limit current +I0 and −I0, respectively, are in each case set by means of the same feedback impedance ZF. In the illustrated exemplary embodiment, a transistor of the BSP 149 type from Siemens Corporation is used in each case for the first and second MOSFETs T1 and T2, respectively. As an alternative, however, the Siemens Corporation transistor BSS 149 could also be used, by way of example. The feedback impedance ZF is purely resistive and has a value of 5.1 Ω. An absolute limit current |I0| of approximately 100 mA is set as a result of this.

The junction or forward resistance of the second nonlinear two-terminal network Z2 illustrated is produced as the series circuit formed by a first drain-source resistance, the feedback impedance ZF and a second drain-source resistance, the first and second drain-source resistances in each case constituting an internal resistance of the first and second MOSFET T1 and T2, respectively. For small signal levels lying within the transition region, the two MOSFETs T1 and T2 are in each case operated in a virtually symmetrical drive region around the zero point of the family of output characteristic curves of the two MOSFETs T1 and T2. For small signal levels, the characteristic curves of the family of output characteristic curves of the two MOSFETs T1 and T2 in each case have a linear gradient corresponding to the drain-source resistance already discussed. A total junction resistance of approximately 10 Ω then results in the present case.

For large signal levels beyond the transition region, as are present in the case of the transmission signal 40 for example, the two MOSFETs T1 and T2 no longer behave symmetrically. Depending on the signal polarity, one always acts as a current limiter and the respective other acts as a diode in the forward region, on account of the backward diode which is an integral part of the respective normally-on MOSFET T1 or T2. In the case of a positive voltage value of the transmission signal 40, the first MOSFET T1 acts as a current limiter, while the second MOSFET T2 is operated via its backward diode and allows the limit current I0 to pass unimpeded. The conditions are exactly reversed for a negative voltage value of the transmission signal 40.

The maximum voltage with which the nonlinear two-terminal network Z2 can be loaded depends on the maximum voltage that is permitted to be applied, in a manner dictated by the design, between the respective drain terminal D1 or D2 and the respective source terminal S1 or S2 of the two MOSFETs T1 and T2, respectively. This voltage is approximately 200 V in the case of the type of transistor chosen.

Figure 7:
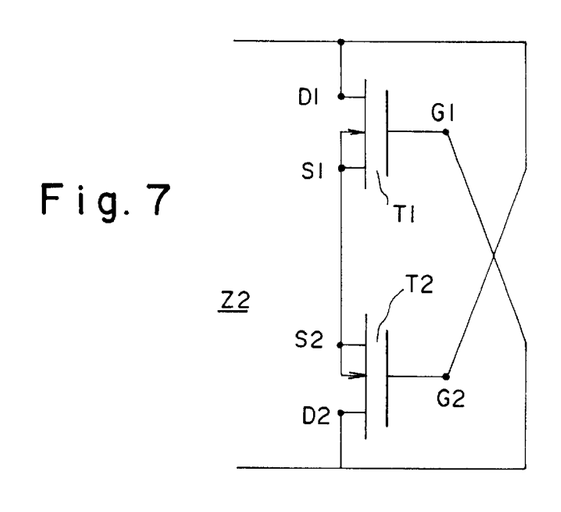
FIG. 7 is a schematic diagram of a further embodiment of the second nonlinear two-terminal network.

FIG. 7 illustrates an alternative embodiment of the second nonlinear two-terminal network Z2. In contrast to the embodiment of FIG. 6, the variant of FIG. 7 does not comprise a separate feedback impedance ZF. Rather the first gate terminal G1 is in this case fed back via a drain-source resistance of the second MOSFET T2 to the first source terminal S1, and the second gate terminal G2 is fed back via a drain-source resistance of the first MOSFET T1 to the second source terminal S2. The corresponding drain-source resistances are thereby formed in each case by the nonlinear resistance of the backward diode of the two MOSFETs T1 and T2. The omission of the feedback impedance ZF means that, on the one hand, the gradient of the characteristic curve in accordance with FIG. 3 in the transition region is increased, that is to say the junction or forward resistance is decreased, but, on the other hand, the second nonlinear two-terminal network Z2 in accordance with FIG. 7 can be operated only with a maximum voltage of approximately 20 V.

The lower operating voltage is due to the maximum permissible gate-source voltage of the MOSFETs T1 and T2 used, which is precisely the voltage value mentioned. The voltage present at the second nonlinear two-terminal network Z2 is dropped virtually completely in one of the two transistors T1 or T2 between the gate terminal G1 or G2, respectively, and the source terminal S1 or S2, respectively. The voltage dropped between gate and source is reduced here merely by the voltage drop across the backward diode of the respective other MOSFET T1 or T2. The design dictates a maximum permissible voltage of approximately 20 V between the gate and the source.

Figure 8:
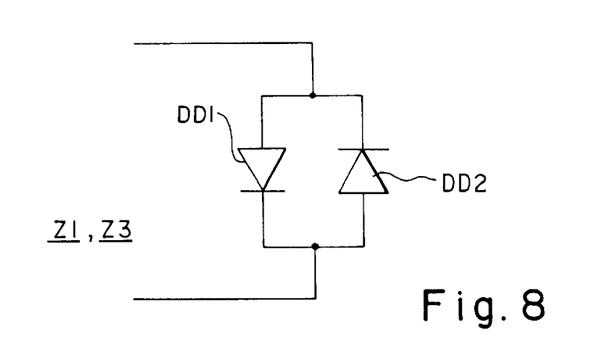
FIG. 8 is a schematic of an embodiment of the first and third nonlinear two-terminal networks.

FIG. 8 illustrates a realization of the first and third nonlinear two-terminal networks having a characteristic curve in accordance with FIG. 2. The embodiment involves a reverse-connected parallel circuit formed by two structurally identical diodes DD1 and DD2. The Siemens diodes with the designation BAV 99 were used for these in the present case.

Figure 9:
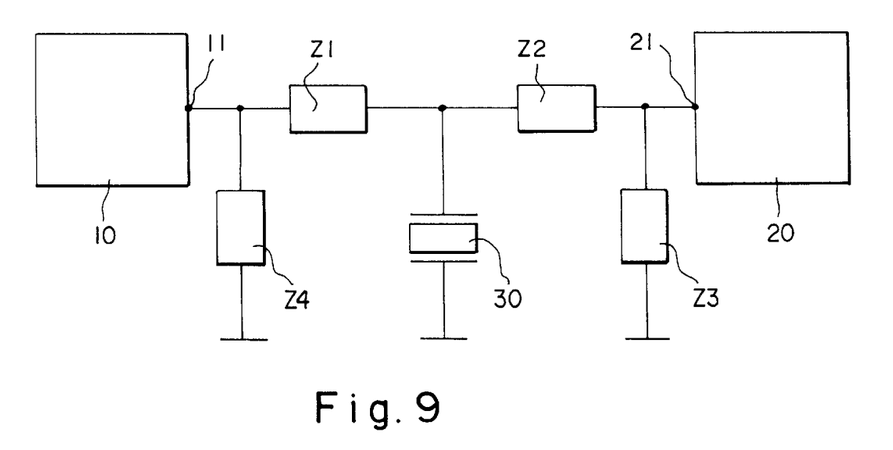
FIG. 9 is a schematic block diagram of a further transmitting/receiving circuit with four nonlinear two-terminal networks.

In addition to the circuit having a total of three nonlinear two-terminal networks Z1 to Z3 as shown in FIG. 1, it is also possible to embody the invention with a total of four nonlinear two-terminal networks. The variant of the transmitting/receiving circuit as shown in FIG. 9 contains a fourth nonlinear two-terminal network Z4, which is connected in parallel with an output 11 of the transmitter 10.

Analogously to the second nonlinear two-terminal network Z2, the fourth nonlinear two-terminal network has a bipolar current-limiting behavior. It is advantageous particularly when the transmitter 10 has an inductive output impedance. This is the result if the final signal level of the transmission signal 40 is set by means of a non-illustrated transformer. The transformer is situated directly at the output 11 of the transmitter 10 for this purpose. In this embodiment, it can happen that a current flow has not yet decayed in a secondary winding of the transformer even though the transmission signal 40 has already been transmitted via the first nonlinear two-terminal network Z1 and the latter has already assumed its high-impedance state again. The energy still stored in the transformer can then flow away only to a limited extent, thereby resulting in a comparatively long decay duration of the transmission signal 40. Connecting the fourth nonlinear two-terminal network Z4 in parallel at the output 11 of the transmitter 10 opens up an additional path for the energy stored in the transformer and, consequently, contributes to reducing the decay time of the transmission signal 40.

I claim:

1. A circuit, comprising:
    a transmitter for transmitting a transmission signal, a transducer connected to said transmitter for receiving the transmission signal, and a receiver having an input connected to said transducer for receiving a reception signal from said transducer;
    a first nonlinear, bipolar voltage-limiting two-terminal network connected between said transmitter and said transducer;
    a second nonlinear, bipolar current-limiting two-terminal network connected between said transducer and said receiver, said second nonlinear, bipolar current-limiting two-terminal network containing a series circuit formed by a first normally-on MOSFET having a first gate terminal, a first source terminal, and a first drain terminal; and
    a third nonlinear, bipolar voltage-limiting two-terminal network connected in parallel with said input of said receiver.

2. The circuit according to claim 1, wherein said transducer is an ultrasonic transducer.

3. The circuit according to claim 1, wherein said transducer has a grounded side.

4. The circuit according to claim 1, wherein the first, second and third nonlinear two-terminal networks are passive two-terminal networks.

5. The circuit according to claim 1, wherein said transmitter has an output, and a fourth nonlinear two-terminal network connected in parallel with said output of said transmitter.

6. The circuit according to claim 5, wherein said fourth nonlinear two-terminal network is a two-terminal network with bipolar current limiting.

7. The circuit according to claim 5, wherein said fourth nonlinear two-terminal network is a passive network.

8. The circuit according to claim 1, wherein said series circuit further comprising a second normally-on MOSFET having a second gate terminal, a second source terminal, and a second drain terminal, wherein said first MOSFET and said second MOSFET are arranged with mutually opposite polarity within said series circuit, and including a feedback via a resistance from said first gate terminal and said second gate terminal to said first and second source terminals, respectively.

9. The circuit according to claim 8, wherein said resistance is a common feedback impedance connected between said first and second source terminals and between said first and second gate terminals and said first and second source terminals.

10. The circuit according to claim 9, wherein said common feedback impedance is an impedance selected from the group consisting of resistive, inductive, capacitive, and arbitrarily complex impedance.

11. The circuit according to claim 8, wherein said first gate terminal is electrically connected to said second drain terminal for feeding back said first gate terminal via a drain-source resistance of said second MOSFET to said first source terminal, and said second gate terminal is electrically connected to said first drain terminal for feeding back said second gate terminal via a drain-source resistance of said first MOSFET to said second source terminal.

12. A method of transmitting a transmission signal to a transducer and for receiving a reception signal from the transducer, which comprises:

coupling a transmission signal of a transmitter to a transducer via a first nonlinear two-terminal network and decoupling the transmission signal from a receiver with a second and a third nonlinear two-terminal network; and coupling a reception signal of the transducer to a receiver via the second and third nonlinear two-terminal networks and decoupling the reception signal from the transmitter with the first nonlinear two-terminal network; and thereby limiting a voltage present at the first nonlinear two-terminal network and a voltage present at the third nonlinear two-terminal network in bipolar fashion; and limiting a current flowing through the second nonlinear two-terminal network in bipolar fashion using a series circuit formed by a normally-on MOSFET having a gate terminal, a source terminal, and a drain terminal.

13. The method according to claim 12, which comprises exciting the transducer with the transmission signal and emitting ultrasound with the transducer.

14. The method according to claim 12, wherein the transducer is connected to system ground.

15. The method according to claim 12, wherein the first, second and third nonlinear two-terminal networks are each purely passive two-terminal networks.

16. The method according to claim 12, which comprises shortening a decay time of the transmission signal at the transmitter with a fourth nonlinear two-terminal network.

17. The method according to claim 16, which comprises limiting a current flowing through the fourth nonlinear two-terminal network in bipolar fashion.

* * * * *